(12) United States Patent  
Pettigrew et al.

(10) Patent No.: US 9,068,997 B2  
(45) Date of Patent: Jun. 30, 2015

(54) ANALYTE EXTRACTION APPARATUS AND METHOD

(75) Inventors: David Michael Pettigrew, Huntingdon (GB); Bo Liu, Cambridge (GB); Peter Georg Laitenberger, Cambridge (GB); Stephen Bates, Cambridge (GB)

(73) Assignee: SPHERE MEDICAL LIMITED, Cambridge (GB)

( * ) Notice: Subject to any disclaimer, the term of this patent is extended or adjusted under 35 U.S.C. 154(b) by 116 days.

(21) Appl. No.: 13/878,820

(22) PCT Filed: Oct. 11, 2011

(86) PCT No.: PCT/GB2011/051958  
§ 371 (c)(1),  
(2), (4) Date: Jul. 24, 2013

(87) PCT Pub. No.: WO2012/049491  
PCT Pub. Date: Apr. 19, 2012

(65) Prior Publication Data  
US 2013/0316464 A1 Nov. 28, 2013

(30) Foreign Application Priority Data

Oct. 15, 2010 (GB) .................................. 1017479.5

(51) Int. Cl.  
*G01N 33/94* (2006.01)  
*G01N 33/50* (2006.01)  
*G01N 33/00* (2006.01)  
*G01N 30/06* (2006.01)  
*G01N 30/24* (2006.01)  
*G01N 30/08* (2006.01)

(52) U.S. Cl.  
CPC ...... *G01N 33/948* (2013.01); *Y10T 436/203332* (2015.01); *Y10T 436/11* (2015.01); *Y10T 436/255* (2015.01); *G01N 30/06* (2013.01); *G01N 30/24* (2013.01); *G01N 2030/067* (2013.01); *G01N 2030/085* (2013.01)

(58) Field of Classification Search  
CPC ...... G01N 33/948; G01N 33/94; G01N 33/50; G01N 33/00; Y10T 436/00; Y10T 436/11; Y10T 436/20; Y10T 436/203332; Y10T 436/25; Y10T 436/255  
USPC ...................... 436/131, 127; 422/50  
See application file for complete search history.

(56) References Cited

U.S. PATENT DOCUMENTS

| | | |
|---|---|---|
| 5,906,742 A | 5/1999 | Wang et al. |
| 6,831,733 B2 | 12/2004 | Petterson et al. |
| 7,247,484 B2 | 7/2007 | Wu et al. |
| 2012/0267259 A1 | 10/2012 | Pettigrew et al. |

FOREIGN PATENT DOCUMENTS

| | | |
|---|---|---|
| WO | WO 2005/048126 A2 | 11/2004 |
| WO | WO 2010/017151 A1 | 2/2010 |

OTHER PUBLICATIONS

Ainashef et al.; Electrochemical Generation of Superoxide in Room-Temperature Ionic Liquids; Electrochemical and Solid-State Letters; 4(11):D16-D18; Nov. 2001.

Araki et al.; Antioxidative properties of probucol estimated by the reactivity with superoxide and by electrochemical oxidation; Chem Pharm Bull (Tokyo); 49(8):943-7; Aug. 2001.

Araki et al.; The mechanism of reaction of ebselen with superoxide in aprotic solvents as examined by cyclic voltammetry and ESR; Chem Pharm Bull (Tokyo); 49(5):541-5; May 2001.

Barr et al.; Propofol dosing regimens for ICU sedation based upon an integrated pharmacokinetic-pharmacodynamic model; Anesthesiology; 95(2); p. 324-333; Aug. 2001.

Beissenhirtz et al.; Comparing an in vitro electrochemical measurement of superoxide scavenging activity with an in vivo assessment of antioxidant potential in Chinese tonifying herbs; Phytother Res.; 18(2):149-53; Feb. 2004.

Beissenhirtz et al.; Immobilized Cytochrome c Sensor in Organic/Aqueous Media for the Characterization of Hydrophilic and Hydrophobic Antioxidants; Electroanalysis; vol. 15, Issue 18, pp. 1425-1435, Oct. 2003.

Campanella et al.; Superoxide dismutase biosensors working in non-aqueous solvent; Fresenius J Anal Chem.; 369(7-8):594-600; Apr. 2001.

Cohen et al.; Quantitative measurement of propofol and in main glucuroconjugate metabolites in human plasma using solid phase extraction-liquid chromatography-tandem mass spectrometry; J Chromatogr B Analyt Technol Biomed Life Sci; 854(1-2); pp. 165-172; Jul. 2007.

Csallany et al.; ?-tocopherol oxidation mediated by superoxide anion I. Reactions in aprotic and protic conditions; Lipids; vol. 27, Issue 3, pp. 195-200; Mar. 1992.

(Continued)

*Primary Examiner* — Christine T Mui  
(74) *Attorney, Agent, or Firm* — Shay Glenn LLP (57) ABSTRACT

Disclosed is an apparatus for automatically extracting i2,6-diisopropylphenol (Propofol), from a complex sample matrix comprising cellular material, e.g. blood, the apparatus comprising a sample reception stage having on output for providing a defined quantity of the complex sample matrix; a mixing stage having a first input in fluidic connection with the output of the sample reception stage, a second input for receiving a lysing agent and an output for providing a mixture of the defined quantity of the complex sample matrix and the lysing agent; a delay stage having an input in fluidic connection with the output of the mixing stage and an output for providing the delayed mixture of the defined quantity of the complex sample matrix and the lysing agent; a filtering stage comprising a sorbent material for mechanically lysing the cellular material, said sorbent material having an affinity for binding Propofol, said filtering stage having an input in fluidic connection with the output of the delay stage; and a controller for controlling the flow rate of the mixture of the defined quantity of the complex sample matrix and the lysing agent through said delay stage. A method for such extraction is also disclosed.

22 Claims, 3 Drawing Sheets

(56) References Cited

OTHER PUBLICATIONS

Dawidowicz et al.; The advantages of cell lysis before blood sample preparation by extraction for HPLC propofol analysis; Biomed Chromatogr; 14(7); pp. 493-497; Nov. 2000.

Ezerskis et al.; Electropolymerization of chlorinated phenols on a Pt electrode in alkaline solution Part I: A cyclic voltammetry study; Journal of Applied Electrochemistry; vol. 31; Issue 10; pp. 1117-1124; Oct. 2001.

Ferreira et al.; Electrode passivation caused by polymerization of different phenolic compounds; Electrochimica Acta; vol. 52, Issue 2; pp. 434-442; Oct. 25, 2006.

Gibbs, H.D.; Phenol tests III. The indophenol test; Journal of Biological Chemistry, 72(2); pp. 649-664; 1927 (year of pub. sufficiently earlier than effective US filing date and any foreign priority date).

Gülçin et al.; Determination of in vitro antioxidant and radical scavenging activities of propofol; Chem Pharm Bull (Tokyo); 53(3):281-5; Mar. 2005.

Herath et al.; Electrochemical investigation of superoxide anion scavenging ability of 1,2,3-triketohydrindene hydrate in aprotic solvents; Electrochimica Acta; vol. 51; Issue 14; pp. 2890-2897; Mar. 15, 2006.

Heyne et al.; Investigation of singlet oxygen reactivity towards propofol; Photochem Photobiol Sci; 2(9):939-45; Sep. 2003.

Kohen et al.; Quantification of the overall reactive oxygen species scavenging capacity of biological fluids and tissues; Free Radic Biol Med.; 28(6):871-9; Mar. 15, 2000.

Korotkova et al.; Study of antioxidant properties by voltammetry; Journal of Electroanalytical Chemistry; vol. 518; Issue 1; pp. 55-60; Jan. 11, 2002.

McGaughran et al.; Rapid measurement of blood propofol levels: a proof of concept study; J Clin Monit Comput.; 20(2):109-15; Apr. 2006.

Miniati, Enrico; Assessment of phenolic compounds in biological samples; Ann Ist Super Sanita; 43(4):362-8; (year of publication is sufficiently earlier than the effective U.S. filing date and any foreign priority date) 2007.

Murphy et al.; The antioxidant potential of propofol (2,6-diisopropylphenol); Br J Anaesth.; 68(6):613-8; Jun. 1992.

Pallagi et al.; Mechanism of the Gibbs reaction. Part 4.1 Indophenol formation via n-chlorobenzoquinone imine radical anions .; The Journal of Organic Chemistry; 64(18); pp. 6530-6540; Aug. 1999.

Plummer GF; Improved method for the determination of propofol in blood by high-performance liquid chromatography with fluorescence detection; J Chromatogr.; 421(1):171-6; Oct. 9, 1987.

Prieto-Simón et al.; Electrochemical biosensors as a tool for antioxidant capacity assessment; Sensors and Actuators B: Chemical; vol. 129, Issue 1, pp. 459-466; Jan. 29, 2008.

Renée et al.; Superoxide protonation by weak acids in imidazolium based ionic 7 liquids; J Phys Chem B.; 113(9):2826-31; Mar. 5, 2009.

Shafer et al.; Pharmacokinetics and pharmacodynamics of propofol infusions during general anesthesia; Anesthesiology; 69(3); pp. 348-356; Sep. 1988.

Svobodové et al.; Colour reaction of phenols with the gibbs reagent. The reaction mechanism and decomposition and stabilisation of the reagent; Microchimica Acta; 67; pp. 251-264; May 1977.

Uebel et al.; Electrochemical determination of 2,6-diisopropylphenol after high-performance liquid chromatography of extracts from serum; J Chromatogr.; 526(1):293-5; Mar. 16, 1990.

Volti et al.; Antioxidant properties of propofol when oxidative stress sleeps with patients; EXCLI Journal; 5:25-32; Apr. 13, 2006.

Pettigrew et al.; U.S. Appl. No. 13/878,815 entitled "Analyte detection method," filed Apr. 11, 2013.

Svobodová et al.; The colour reaction of phenols with the Gibbs reagent; Microchimica Acta; 70(II/3-4); pp. 197-211; May 1978.

ANALYTE EXTRACTION APPARATUS AND METHOD

FIELD OF THE INVENTION

The present invention relates to a method and apparatus for improving the automation of cell lysis for use in the extraction and measurement of analyte concentrations in biological samples. In particular, this invention provides a means for automatically diluting and lysing blood cells prior to propofol extraction and analysis.

BACKGROUND OF THE INVENTION

Modern healthcare relies extensively on a range of chemical and biochemical analytical tests on a variety of body fluids to enable diagnosis, therapy and management of disease. Medical and technological advances have considerably expanded the scope of diagnostic testing over the past few decades. Moreover, an increasing understanding of the human body, together with the emergence of technologies, such as microsystems and nanotechnology, are expected to have a profound impact on diagnostic technology.

Increasingly, diagnostic tests in hospitals are carried out at the point-of-care (PoC), in particular, in situations where a rapid response is a prime consideration and therapeutic decisions have to be made quickly. Despite recent advances in PoC testing, several compelling needs remain unmet. In particular, many assay methods require extensive pre-treatment of a complex sample matrix (such as whole blood) prior to analysis. For example, many sample preparation methods involve the disruption (lysis) and/or removal (filtration/centrifugation) of blood cells. Consequently, these steps are usually performed manually by highly skilled laboratory personnel. This requirement precludes the use of such assays in a PoC setting. There is therefore a strong unmet need to automate whole blood sample preparation methods. The detection and measurement of analyte levels in biological media (e.g. blood, plasma, saliva, urine) is often difficult due to the association of the analyte with components of the sample matrix (e.g. plasma proteins and lipid membranes). The free (unbound) molecule concentration (which can be in the picomolar range) is often below the sensitivity limits of the most commonly used measurement techniques (e.g. electrochemical, optical). Furthermore, several endogenous interfering compounds may be present and often need to be removed before analysis. To avoid these problems, state of the art methods for analyte measurement in biological samples usually incorporate one or more sample preparation steps that are intended to alter the composition of the sample being tested to make it compatible with the requirements of the detection system being employed (using e.g. optical, electrochemical, mass measurement techniques). Sample preparation methods can include, but are not limited to; antibody labelling, cell disruption (lysis) by chemical, mechanical or osmotic means, metered dilution into an alternative solvent, solid phase extraction, filtration, centrifugation and/or evaporation.

There are numerous examples in the prior art of assays that employ automated sample preparation from whole blood, including lateral flow immunoassays for plasma/cell separation, as for instance disclosed in U.S. Pat. No. 5,906,742, optical haemoglobin assays as for instance disclosed in U.S. Pat. No. 6,831,733 and haematology analysers utilizing cell lysis as for instance disclosed in U.S. Pat. No. 7,247,484.

However, many other biological assays require extensive manual sample preparation steps prior to analysis. For example, an established "gold standard" HPLC assay for the measurement of the anaesthetic drug propofol in whole blood usually involves dilution of a whole blood sample into a known volume of organic solvent, followed by centrifugation and injection of a known volume of the supernatant into an HPLC device for analysis, as disclosed by G. F. Plummer et al. in Improved method for the determination of propofol in blood by high-performance liquid chromatography with fluorescence detection," *Journal of Chromatography*, vol. 421, no. 1, p. 171, 1987 and by R. A. Uebel et al. in "Electrochemical determination of 2,6-diisopropylphenol after high-performance liquid chromatography of extracts from serum," *Journal of Chromatography*, vol. 526, no. 1, pp. 293-295, March 1990.

To date, no method for automating these sample preparation steps has been established.

The complex and time-consuming nature of the sample preparation steps involved in many biological assays mean that they are routinely performed by a very small number of specialist laboratories. In many cases, there is a clear need to develop assays with automated sample preparation modules incorporated. This would enable the delivery of an un-processed sample to the device, which in turn would enable measurement and clinical intervention close to real time and at the Point of Care (PoC).

A partially automated method for detecting and measuring propofol in biological samples, such as whole blood, has been described by McGaughran et al. in "Rapid measurement of blood propofol levels: A proof of concept study," *Journal of Clinical Monitoring and Computing*, vol. 20, no. 5, pp. 381-381, 2006. The assay involves manual preparation of the blood sample, before introduction to an instrument that performs the remainder of the assay automatically. The assay is performed in the following way: First, a whole blood sample is osmotically lysed by dilution with deionised water at a ratio of 1:2. Then, the sample is transferred to a syringe and injected into the measurement device via a 1 μm syringe filter. The purpose of the filter is to mechanically lyse the remainder of the erythrocytes, erythrocyte ghosts ("empty" erythrocytes with an intact membrane) and large membrane fragments. It is essential to avoid injecting large cellular aggregates into the measurement system, which will potentially cause blockages and/or interfere with the extraction of the propofol from the sample. The automated portion of the assay involves delivery of a metered volume of the sample to a solid phase extraction (SPE) column, which extracts the propofol from the sample. After a series of washing steps, the propofol is eluted into the optical detection chamber using a metered volume of acetonitrile and reacted with a phenol-specific (Gibbs) reagent, namely 2,6 dichloroquinone-4-chloroimide, to produce a strongly coloured indophenol product. Absorption spectroscopy is used to measure the concentration of the coloured product, which is related to the original concentration of propofol in the whole blood sample.

The method described above has several advantages over the existing HPLC ones such as disclosed by G. F Plummer et al. and R. A. Uebel et al. For example, the device is much easier to use and maintain than the more general purpose HPLC instrument. Also, the device is significantly cheaper than HPLC and requires much smaller reagent volumes per measurement. Moreover, typical measurement times are much faster at approximately 3 to 5 minutes. Finally, the instrument has a much smaller footprint than the equivalent HPLC device, which is an important consideration for a busy clinical laboratory.

Unfortunately, several factors mean that the assay is unsuitable for routine clinical laboratory or PoC use. First, the lysis step requires accurate and precise metering of the sample and diluent volumes; this is a significant source of user error. Second, the extra blood manipulation presents an additional biohazard risk to the user. Third, as reported by A. L Dawidowicz et al. in "The advantages of cell lysis before blood sample preparation by extraction for HPLC propofol analysis," *Biomedical Chromatography*, vol. 14, no. 7, pp. 493-497, 2000, as a significant (~30-40%) proportion of the propofol is partitioned into cells retaining cell membranes on the syringe filter may result in a significant removal of the propofol from the sample before introduction to the instrument. This means that the final propofol concentration is not necessarily representative of the "true" concentration of propofol in the original whole blood sample. Overall, these factors mean the device is restricted to highly trained laboratory personnel in specialised laboratories. It is therefore desirable to incorporate the lysis (dilution and filtration) step into the instrument, so that the user can inject the blood directly into the device without prior sample preparation.

Despite the relative simplicity of the manual sample preparation protocol in the Gibbs/indophenol method for propofol detection, no methods or apparatus exist in the prior art which are compatible with automation of the lysis technique described above. In particular, handling small volumes of whole (rather than diluted) blood in a fluidic system is challenging. Reliable mixing of the blood with the lysing agent (water) in a defined ratio using narrow bore tubing is very difficult to achieve due to the variable viscosity of blood and the propensity of erythrocytes to stick to the walls of the tubing. The loss of erythrocytes is particularly problematic as a significant proportion of the drug (~30-40%) is bound to these cells, thereby reducing the recovery by the SPE column. Also, the mixing of the blood with the lysing agent would typically require the use of two pumps which increases instrument complexity and cost. Incorporating an appropriate inline filter with enough capacity to perform the mechanical lysis step without blocking is difficult, as a large extra dead volume will be introduced into the system. This extra dead volume will lower the precision of the dispensed volumes, which in turn will introduce errors in the measured propofol concentration. Moving to harsher, detergent and/or acid-based lysis reagents such as disclosed in U.S. Pat. No. 7,247,484 would remove the erythrocyte ghosts and the larger membrane fragments and has the potential to remove the need for inline filtration entirely. However, these same detergents would interfere with the extraction of propofol by the reverse phase extraction column and produce errors.

SUMMARY OF THE INVENTION

The present invention seeks to provide an apparatus and method for automating the dilution and/or lysis of biological samples prior to assaying one or more analyte level(s) in the same sample. In particular, the present invention seeks to provide an apparatus and method for automatically diluting and lysing a whole blood sample prior to solid phase extraction and measurement of the anaesthetic drug propofol.

In accordance with an aspect of the present invention, there is provided an apparatus for automatically extracting 2,6-diisopropylphenol (Propofol) from a complex sample matrix comprising cellular material, the apparatus comprising a sample reception stage having on output for providing a defined quantity of the complex sample matrix; a mixing stage having a first input in fluidic connection with the output of the sample reception stage, a second input for receiving a lysing agent and an output for providing a mixture of the defined quantity of the complex sample matrix and the lysing agent; a delay stage having an input in fluidic connection with the output of the mixing stage and an output for providing the delayed mixture of the defined quantity of the complex sample matrix and the lysing agent; a filtering stage comprising a sorbent material for mechanically lysing the cellular material, said sorbent material having an affinity for binding Propofol, said filtering stage having an input in fluidic connection with the output of the delay stage; and a controller for controlling the flow rate of the mixture of the defined quantity of the complex sample matrix and the lysing agent through said delay stage.

The inventors have realised that applying the lysis inside the apparatus overcomes one of the fundamental problems that state of the art solutions in analyte extraction suffer from.

In the prior art, and in particular in the method of McGaughran et al., samples are typically diluted and filtered prior to insertion of a metered portion of the diluted sample into a detection apparatus, which causes cellular materials including cellular debris to be caught on the filter. This step is necessary to ensure that the internals of the detection apparatus do not become contaminated with such cellular material, as such material would interfere with the correct operation of the device, e.g. through blockage of fluid channels. However, the drawback of this filtering step is that any analyte of interest that has been captured by the cellular material, e.g. through absorption into the cells, is also filtered out, which introduces significant inaccuracies in the concentration of the analyte of interest in the filtrate. In other words, the sample composition is altered in an unknown manner by the filtration. More importantly, in the method of McGaughran et al., the amount of lysing agent has to be determined in an accurate manner to ensure that the dilution rate of the complex sample matrix is well-defined. This is necessary because a metered portion of the sample diluted by the lysing agent is used for insertion into a detection apparatus, such that the dilution factor must be known to a high degree of accuracy to allow correlation of the measurement of the absolute amount of the analyte of interest in this metered portion to the original concentration of the analyte of interest in the complex sample matrix. For these reasons, the method of McGaughran et al. is rather sensitive to measurement errors.

This problem is solved by the present invention by the combining osmotic and mechanical lysis inside the apparatus and, preferentially achieving the mechanical lysis by passing the diluted sample across a sorbent with affinity for the analyte of interest. This approach enhances the efficiency of the release of Propofol onto the sorbent. In addition, the apparatus is constructed such that any sample material being accumulated on top of the sorbent is still available for the subsequent Propofol extraction and detection/measurement.

This approach allows a more efficient extraction of Propofol from the complex sample matrix, such that the extracted amount of Propofol accurately reflects the concentration of Propofol in the complex sample matrix. In other words, the sorbent/filter in the apparatus of the present invention has a dual function of extracting as well as assisting in the lysis of the cellular material, such that Propofol can be extracted from the degraded cellular material prior to passing the resultant filtrate onto a detection unit. This implies a reduction in the number of filtration devices compared to the McGaughran et al. as the mechanical lysing and analyte extraction are combined in a single filtering stage, which reduces the footprint of the overall apparatus. In addition, the lysed cellular material on the filter bed can be exposed to the eluent, contrary to the external filter used in the method of McGaughran et al., which has the advantage that a more effective extraction of Propofol from the sorbent material is achieved, thus improving the accuracy of a subsequent determination of the concentration of Propofol in the complex sample matrix.

In addition, the novel apparatus provides for more efficient use as it allows the injection of whole blood samples into the instrument without the requirement for pre-treatment or dilution. This has the important advantage that the actual volume of lysing agent used does not need determining, as the metering is performed on the actual complex sample matrix, such that the amount of Propofol extracted from the sample diluted by the lysing agent directly corresponds to the amount of Propofol present in the complex sample matrix; i.e. the amount of lysing agent used is irrelevant other than for the purpose of ensuring that the cellular material is sufficiently destabilized, e.g. ruptured.

Furthermore, the lysis can be achieved without the use of reagents which interfere with the extraction of the Propofol from the sample.

In an embodiment, the sample reception stage comprises a metering device for extracting a known quantity of a complex sample matrix received at the input of the sample reception stage. This reduces the required amount of reagents such as the lysis agent as the sample evaluation is performed on a portion of the sample only. The metering device may comprise a rotary valve.

In an embodiment, the delay stage comprises a delay line of predefined length, such that for a given flow rate the dwell time of the diluted sample is well-defined. Such a delay line preferably comprises flexible tubing as this is a cost-effective way of implementing such a delay line.

In an embodiment, the apparatus of further comprises a fluid reservoir in fluid connection with the filtering stage for providing the filtering stage with a washing agent for removing materials that would interfere with the subsequent extraction of Propofol from the sorbent material, thus further improving the accuracy of the Propofol detection with the apparatus.

Preferably, the filter stage is comprised in a solid phase extraction (SPE) cartridge such that the apparatus can be easily reused by simply replacing the SPE cartridge.

Suitable sorbent materials that demonstrate an affinity with Propofol include reverse phase sorbent materials such as C8, C12, C18 or Strata-X.

In an embodiment, the filter stage further comprises an output, the apparatus further comprising an analyte detection stage having an input in fluidic connection with the output of the filter stage. This has the advantage that the amount of Propofol may be detected with the same apparatus, thus avoiding the need to transfer the filtered sample to a separate measurement device, which introduces the risk of errors.

The analyte detection stage may comprise a detection module selected from the group comprising an electrochemical detector, a fluorescence detector, a gravimetric detector and a spectrophotometer for measuring an absorption spectrum.

In an embodiment, the apparatus further comprises an additional filter in between the delay stage and the filtering stage to further improve the separation of the Propofol from the complex sample matrix.

In accordance with another aspect of the present invention, there is provided a method of extracting 2,6-diisopropylphenol (Propofol) from a complex sample matrix comprising cellular material, the method comprising providing a known quantity of the complex sample matrix; diluting said known quantity with a lysing agent, said lysing agent having an osmotic pressure lower than the osmotic pressure of the cellular material; and subsequently feeding the diluted known quantity through a filter after a predetermined amount of time to separate Propofol from the destabilized cellular material by selectively adhering the analyte of interest to the sorbent material.

BRIEF DESCRIPTION OF THE EMBODIMENTS

Embodiments of the invention are described in more detail and by way of non-limiting examples with reference to the accompanying drawings, wherein.

DETAILED DESCRIPTION OF THE DRAWINGS

It should be understood that the Figures are merely schematic and are not drawn to scale. It should also be understood that the same reference numerals are used throughout the Figures to indicate the same or similar parts.

The invention can be applied to situations where an analyte of interest such as Propofol has to be extracted from a complex, in particular a biological, sample. It is in particular applicable to the extraction of chemical species from blood samples. In these samples, some of the analyte or analytes of interest contained in the sample will typically be bound to constituents of the sample, for example, blood cells. In order to measure the concentration of the analyte or analytes in the sample, the analyte or analytes will often have to be extracted from these constituents during a sample preparation step prior to the actual detection or measurement step. While the invention will be illustrated primarily with respect to blood samples, it is equally applicable to other samples containing cells or similar structures. In general, embodiments of the present invention employ a combination of dilution, osmotic lysis and mechanical lysis to break up cells and make the analyte of interest bound to the cell components available for analysis. In order to achieve this aim, the sample is initially diluted using a lysing agent, for example de-ionised water, solutions containing detergents, urea, acids or combinations thereof; the actual choice of lysing agent will depend on the characteristics of the sample and suitable agents are known to those trained in the art of cell lysis. The dilution step will result in the cells contained in the blood sample taking on components of the lysing agent (e.g. water) and therefore swelling or breaking up. The cells contained in the sample will therefore either burst and release their content or will be in a more fragile state (e.g. in the form of erythrocyte ghosts in the example of osmotic lysis by the dilution into water).

Following a delay stage (typically of the order of seconds to several minutes), the diluted sample will then be passed through a solid phase extraction cartridge. An additional pre-filter may also be incorporated just before the SPE cartridge. The advantage of such a pre-filter over the prior art is that it may also be used for mechanical lysis and exposed to subsequent extraction of the analyte of interest using a suitable eluent as it is placed in the fluid lines of the apparatus of the present invention.

The shear forces introduced by the action of the SPE cartridge or the filter/SPE cartridge combination serves to increase the lysis efficiency by breaking up the intact erythrocytes, erythrocyte ghosts and other cell fragments that remained after the dilution into the lysis agent. The composition of the sorbent in the cartridge or pre-filter is chosen such that it is able to bind the analyte of interest in preference to the components of the sample matrix. The combined action of diluting the sample with a lysing agent and lysing the remaining cells by shear force increases the availability of the analyte of interest for extraction onto the sorbent of the solid phase extraction column.

There is also the possibility of some components of the sample matrix (e.g. unlysed cells or fragments thereof) being accumulated on top of the sorbent bed or pre-filter and not being passed through the sorbent. In a subsequent step, the sorbent cartridge is washed using one or more suitable washing agent(s). The choice of washing agent will depend on the analyte of interest; the washing agent should preferentially remove interferents from the sorbent and sample material accumulated on top of the sorbent bed, while leaving the analyte of interest bound to the sorbent or filter material.

Additionally, in one embodiment of the invention, the washing agent will assist in the break up of the accumulated cell debris on the sorbent bed and increase the availability of the analyte for extraction.

Following the washing step, the analyte of interest is eluted from the sorbent, pre-filter and/or the material accumulated on top of the sorbent/filter material. This elution step employs a suitable extraction agent, which is able to dissolve the analyte of interest from the sorbent or filter material and also from the material left behind on top of the sorbent/filter. The eluent is then passed into a detection chamber where the analyte of interest is detected or the amount of the analyte of interest in the eluent is quantified. A range of detection or measurement techniques are available depending on the analyte of interest. For example, in the case of propofol, colorimetric, optical, fluorescent or electrochemical detection techniques may be used.

Figure 1:
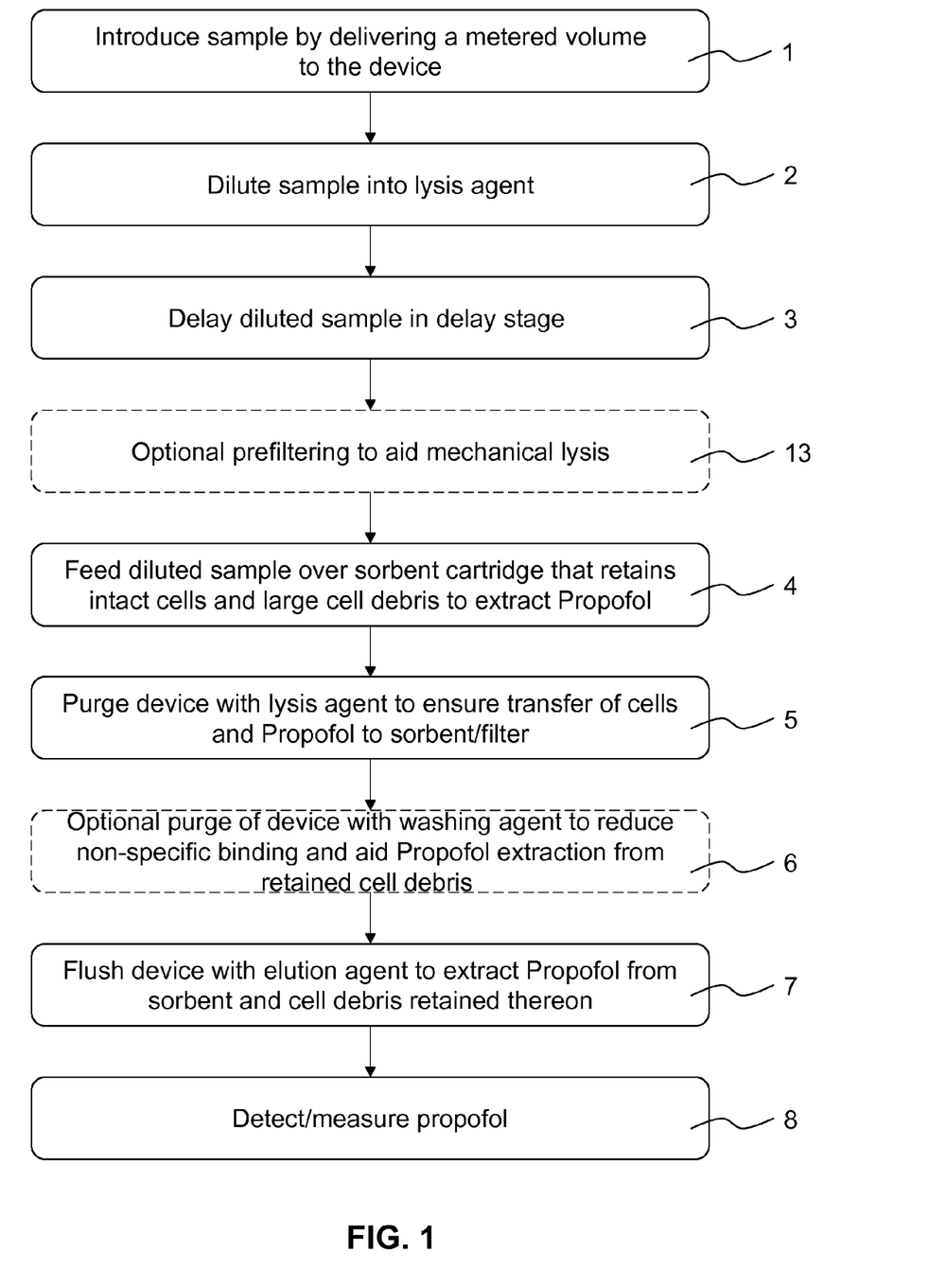
FIG. 1 schematically depicts an embodiment of the measurement method of the present invention incorporating the novel sample preparation approach.
Figure 2:
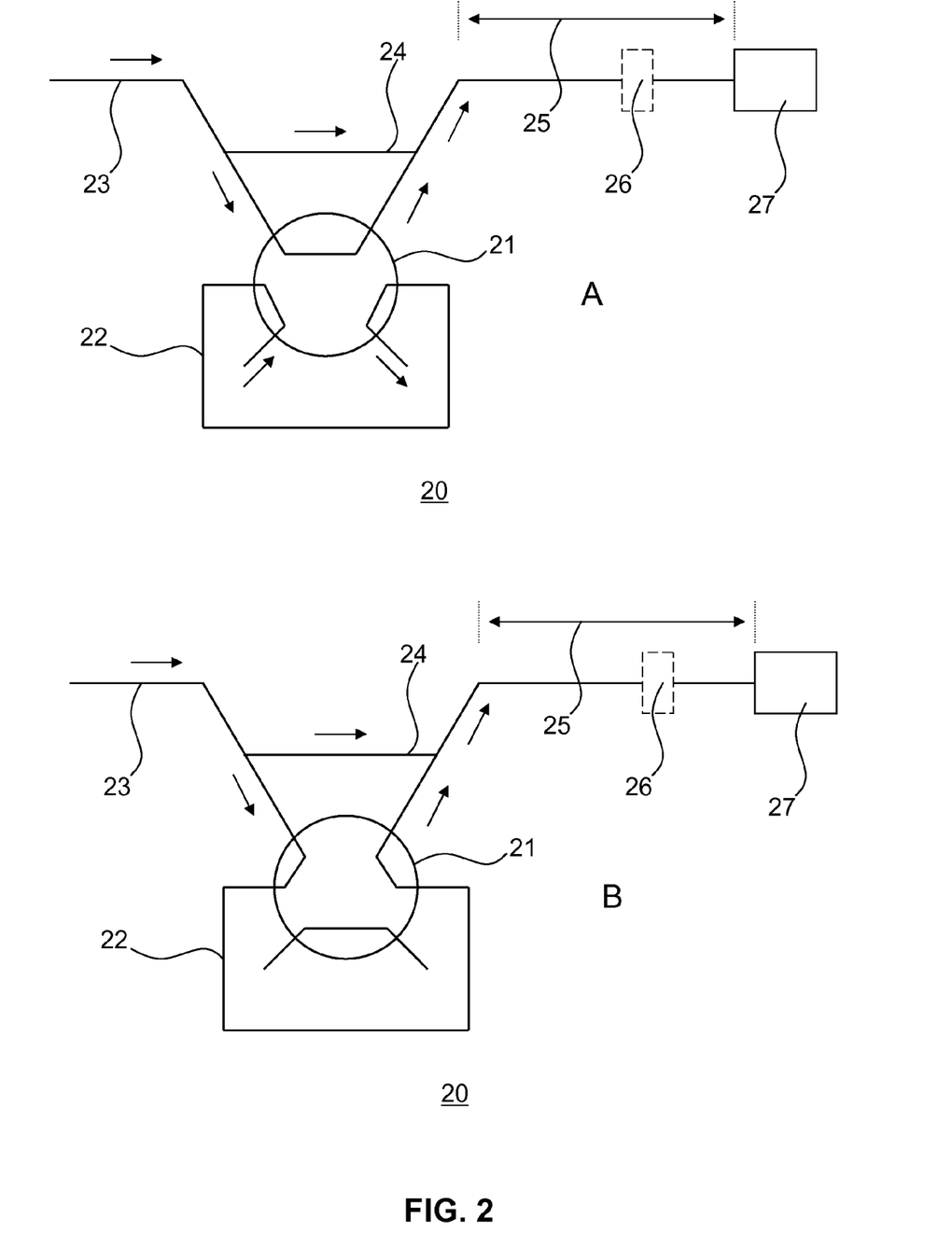
FIG. 2 schematically depicts an embodiment of the device of the present invention incorporating the novel sample preparation method.

One non-limiting embodiment of the present invention is described in more detail in FIG. 1 in conjunction with FIG. 2, which shows an apparatus 20 capable of implementing this method. This embodiment comprises the following steps, some of which are optional as indicated by the dashed boxes in FIG. 1:

1. Introducing a Sample Volume to the Fluidic System

The sample introduced into the apparatus 20 in any suitable manner, e.g. either in a manual or automated fashion.

If concentration measurements are being made by the apparatus 20, it is preferred that a known volume of this sample is made available for further processing by the apparatus 20. Metering a known volume from the sample may be achieved using a sample metering module 21. An example suitable implementation of a method of delivering a known volume includes, but is not limited to, a 6 port, 2 position rotary valve connected to the fluidic system. This valve can be used to switch a length of tubing 22 containing a known volume of the sample of interest into the rest of the fluidic system. This is shown in FIG. 2 as valve position A. Other methods of introducing a known sample volume to a fluidic system will be known to those who are skilled in the art.

Alternatively, a known volume of sample may be introduced either manually or automatically in the first place.

In one particular embodiment, the sample is a sample of body fluids, for example, blood, urine, saliva, cerebral fluids and so on.

In a preferred embodiment of the invention, the sample contains the drug propofol as the analyte of interest, as the inaccurate determination of this drug in such samples can be life-threatening, with the method and the device of the present invention being able to extract propofol from such samples with unparalleled accuracy.

2. Dilution of the Sample into an Lysing Agent

The blood sample or parts thereof, for example, the metered volume of the sample, are subsequently mixed with a lysing agent, which may be introduced into the apparatus 20 via tubing 23. The lysing agent is chosen dependent on the sample and the subsequent extraction step. It can, for example, be de-ionised water, aqueous salt solutions with an osmolarity lower than that of the sample, solutions containing ammonium chloride, detergents, urea, acids or combinations thereof. In situations where the analyte of interest (Propofol) is subsequently to be extracted by reverse phase, osmotic lysis by dilution into deionised water is preferred.

The dilution itself may be achieved through the use of a known length of tubing that bypasses the sample metering module, such as the tubing 24 shown in FIG. 2. The relative resistances of the sample metering and bypass lines are chosen to allow for dilution of the sample, for example a dilution between a 1-fold and 100-fold dilution of the sample (preferably 15-fold). The exact dilution of a given sample will vary depending on its viscosity. Methods of tuning the relative resistances will be known to those who are skilled in the art, and may include, but are not limited to, controlling the length and internal diameter of the tubing and the incorporation of a flow restrictor. Such principles are known per se e.g. from the field of microfluidics and will not be explained in further detail for the sake of brevity only.

3. Providing Time for the Sample and the Lysis Agent to Mix and React with Each Other In order to enable the lysis agent and the sample to interact with each other, the diluted sample is given some time before it is passed to the mechanical lysis stage 27 in FIG. 2. This time period depends on the sample being investigated and the nature of the lysis method being employed, but is preferentially of the order of one second to several minutes. This period should be sufficiently long for any cells contained in the diluted sample to be fragile enough for the mechanical lysis stage.

This delay period may be generated by a delay stage, such as delay stage 25 as shown in FIG. 2. This delay stage 25 preferably consists of a defined length of tubing, which, in conjunction with a controlled rate of fluid flow, allows the sample to incubate for a period of time.

4. Mechanical Lysis of the Diluted Sample

After the delay stage 25, the diluted sample is passed across a mechanical lysis stage 27. The purpose of this mechanical lysis stage 27 is to mechanically lyse (break up) the remainder of the cells, the erythrocyte ghosts and the cell membrane fragments by shear forces. The primary purpose of this step is to facilitate the release of the analyte of interest, preferably Propofol, from the cells, cell components and cell membranes, thereby making it more available for subsequent extraction onto the sorbent. The secondary purpose of this stage is to ensure that large intact cells and cell fragments that remain after the initial chemical/osmotic and mechanical lysis steps are retained until they can be broken up sufficiently for efficient analyte extraction from them during subsequent steps (e.g. steps 6-8).

In one preferred embodiment, the mechanical lysis stage 27 consists of a solid-phase extraction cartridge containing a suitable sorbent. The sorbent may be in powdered or in co-sintered form. It may be held in place using a suitable frit. Preferably, the solid phase extraction sorbent should also be capable of extracting the analyte of interest from the lysate. In another embodiment, a filter 26 or a combination of a filter 26 and a solid phase extraction sorbent may be used, with the filter 26 providing a pre-filtering step 13 to aid the mechanical lysis by also retaining intact cells and large cell fragments. Porous materials, including, but not limited to, glass/metallic/polymer fibres, powders or sintered polymer membranes may be used as filters for the mechanical lysis. Other methods of producing porous materials will be known to those who are skilled in the art. Passing the diluted sample through the sorbent and/or porous material will apply shear forces to the cells and cell fragments which will break up the cells. Other methods of applying shear force will be known to those who are skilled in the art.

The diluted and lysed sample is then brought into contact with a suitable sorbent or filter material. The composition of the sorbent or filter material is chosen such that it is able to selectively bind the analyte of interest, i.e. Propofol, in preference to the diluted and lysed sample. The purpose of this step is to extract the analyte of interest from the sample and bind it to the sorbent or filter material.

In one embodiment of the invention, the sorbent or filter 26 and the mechanical lysis stage 27 are combined in one unit. In a preferred embodiment of the invention, the sorbent or filter is used as the porous material in the mechanical lysis stage.

For example, in the case of Propofol being the analyte of interest, a reverse-phase sorbent cartridge is preferred, made from materials known to those trained in solid phase extraction and including materials, such as C18, C8 and Strata-X. Other materials that can be used for the extraction of Propofol include, but are not limited to, molecularly imprinted polymers (MIPs) or other polymers which have the ability to bind propofol.

In a preferred embodiment of the invention, the sorbent is contained in a solid-phase extraction cartridge.

5. Purging of the Sample Metering and Bypass Sections

After all the diluted sample has been transferred to the mechanical lysis/analyte extraction module via the delay stage, the sample metering, bypass, delay and mechanical lysis sections can then be flushed with a large excess of the lysing agent to ensure that all sedimented cells are purged from these lines and transferred to the extraction stage. To this end, the valve 21 is placed in position B as shown in FIG. 2.

6. Optional Washing Step

The sorbent cartridge and/or filter may then be washed using one or more suitable washing agent(s). The purpose of this washing step is to remove any substance which may interfere with the subsequent detection of the analyte of interest from the material adsorbed in the sorbent cartridge or filter. Additionally, this washing step can contribute to the lysing of the cells absorbed on top of the sorbent and/or filter. In the case of propofol being the analyte of interest, suitable washing agents include water or a solution of methanol in water, typically with a methanol:water ratio of 1:1 to 1:10.

7. Extraction of the Analyte of Interest from the Sorbent or Filter

Standard techniques are then used to extract the analyte of interest from the sorbent or filter and the sample materials left behind on top of the sorbent and/or filter. For example, a known volume of a suitable solvent which preferentially dissolves/binds the analyte of interest with respect to the sorbent and/or filter may be passed through the sorbent and/or filter to remove the analyte of interest from the sorbent and/or filter. These techniques will be known to those who are skilled in the art.

In the case of propofol being the analyte of interest, acetonitrile is the preferred solvent for extraction; other suitable extraction agents and methods of extraction are known to those trained in the art of solid phase extraction.

8. Detection or Concentration Measurement of the Analyte of Interest in the Eluent The eluent from the sorbent and/or filter is passed into a detection stage where the concentration of the analyte in the extract, and hence the original concentration in the blood sample, can then be determined using a suitable detection system. The detection system required will vary depending on the analyte of interest.

In the case of propofol, the preferred detection method is as described by McGaughran et al. Other suitable methods for analyte detection may include, but are not limited to, electrochemical, fluorescent or gravimetric approaches. Other methods of detection will be known to those who are skilled in the art.

The automated sample preparation technique of the present invention has significant advantages over the prior art; these advantages are most readily demonstrated in the case of the propofol measurements used as a preferred embodiment of the invention.

Firstly, the system enables flushing the entire contents of the original blood sample over the SPE column 27. This means that no analyte is lost by the aggregation of cells, or cellular debris on a filter before measurement, as was the case in the Propofol measurement method proposed by McGaughran et al.

In addition, the dilution of the sample does not need to be precisely controlled, since all the diluted sample is passed over the sorbent. In the prior art, only a portion of the diluted sample was exposed to the SPE sorbent, creating a potential source of extra error. In addition, using the SPE sorbent as a mechanical lysing agent enhances the efficiency of the release of Propofol onto the sorbent.

Example

The method of the present invention will now be described in further detail by way of the following non-limiting example. In this example, the anaesthetic drug Propofol is detected in an apparatus according to FIG. 2 from whole blood using solid phase extraction (SPE) followed by a Gibbs reaction and detection by absorption spectroscopy. Established measurement protocols for low propofol concentrations rely on time consuming and complex HPLC-based assays. The low complexity and cost of the technique, combined with the convenience in using whole blood as the starting material of the assay, enables a propofol assay that can be performed in a near patient setting.

A blood sample (preferably 1 ml), which contains a known concentration of propofol, is injected into the apparatus 20 shown schematically in FIG. 2. A known volume of blood is taken from the injected sample using a sample loop 22 and a 6 port, 2 position rotary valve 21 connected to the fluidic system. The blood volume contained in the sample loop 22 is then flushed towards a solid phase extraction cartridge 27 using deionised water. During this transfer the blood is mixed with an excess of water, preferentially in a ratio of blood to water of 1:15. Prior to arriving at the solid phase extraction cartridge 27, the diluted sample is passed through a delay stage 25 which consists of a length of tubing. The flow rates and pump flow rates are adjusted to ensure that the sample spends about 3 seconds in this delay stage. The diluted sample is then passed through a SPE column. The sample loop 22, delay stage 25 and column are subsequently washed with preferably 1.5 ml of deionised water and preferably 1.5 ml of a 1:1 mixture of water and methanol to flush any remaining sample constituents onto the SPE cartridge 27 and to remove weakly bound impurities. The propofol extract is then eluted from the SPE column using a known volume (preferably 0.75 ml) of acetonitrile. The solid phase extraction of Propofol into acetonitrile has been detailed by McGaughran et al. The eluent from the SPE column is then transferred to an optical absorption measurement cell. This measurement is described by McGaughran et al.

This approach enables very accurate concentration of propofol in the blood sample injected into the apparatus 20.

Figure 3:
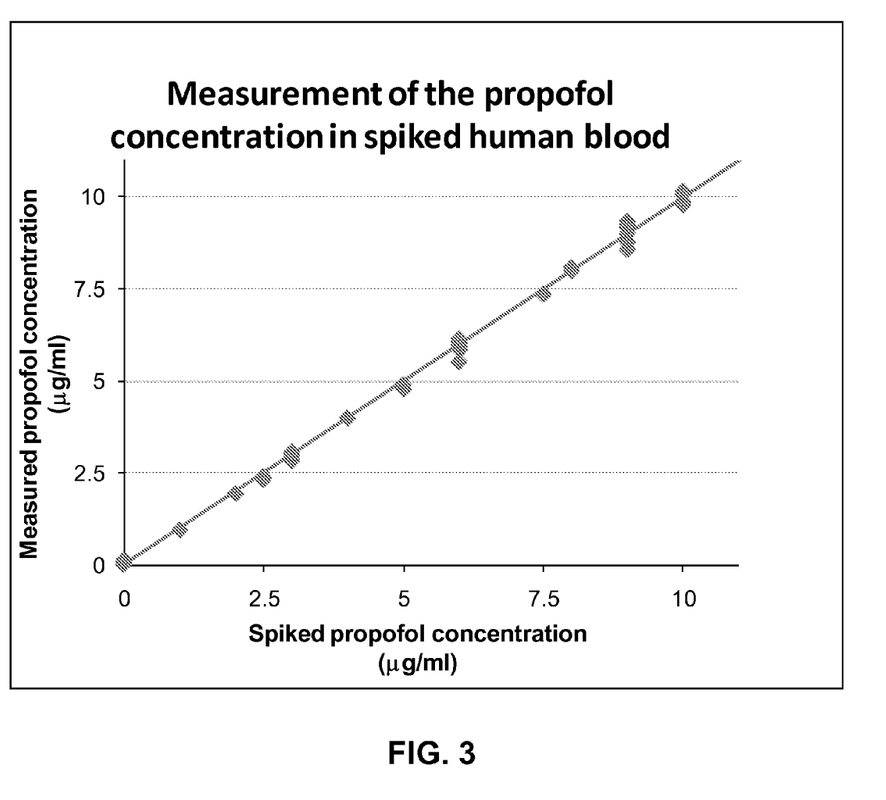
FIG. 3 depicts a graph of the Propofol concentration measurement method using the novel sample preparation approach.

FIG. 3 shows a comparison of the Propofol concentration measured using the apparatus 20 equipped with the sample preparation method of the present invention and the expected propofol concentration in the sample (this concentration expectation is based on the amount of Propofol spiked into the blood sample prior to introducing the blood sample into the apparatus 20).

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An apparatus for automatically extracting 2,6-diisopropylphenol (Propofol) from a complex sample matrix comprising cellular material, the apparatus comprising:
   a sample reception stage having an output for providing a defined quantity of the complex sample matrix;
   a mixing stage having a first input in fluidic connection with the output of the sample reception stage, a second input for receiving a lysing agent and an output for providing a mixture of the defined quantity of the complex sample matrix and the lysing agent;
   a delay stage having an input in fluidic connection with the output of the mixing stage and an output for providing the delayed mixture of the defined quantity of the complex sample matrix and the lysing agent;
   a filtering stage comprising a sorbent material for mechanically lysing the cellular material, said sorbent material having an affinity for binding Propofol, said filtering stage having an input in fluidic connection with the output of the delay stage; and
   a controller for controlling the flow rate of the mixture of the defined quantity of the complex sample matrix and the lysing agent through said delay stage.

2. The apparatus of claim 1, wherein the sample reception stage comprises a metering device for extracting a known quantity of a complex sample matrix received at the input of the sample reception stage.

3. The apparatus of claim 1, wherein the delay stage comprises a delay line of predefined length.

4. The apparatus of claim 1, further comprising a fluid reservoir in fluid connection with the filtering stage for providing the filtering stage with a washing agent for removing materials that would interfere with the subsequent extraction of Propofol from the sorbent material.

5. The apparatus of claim 1, wherein the filter stage is comprised in a solid phase extraction cartridge.

6. The apparatus of claim 1, wherein the sorbent material is a reverse phase sorbent material.

7. The apparatus of claim 1, wherein the filter stage further comprises an output, the apparatus further comprising an analyte detection stage having an input in fluidic connection with the output of the filter stage, wherein the analyte detection stage comprises a detection module selected from the group comprising an electrochemical detector, a fluorescence detector, a gravimetric detector and a spectrophotometer for measuring an absorption spectrum.

8. The apparatus of claim 1, further comprising an additional filter in between the delay stage and the filtering stage.

9. A method of extracting 2,6-diisopropylphenol (Propofol) from a complex sample matrix comprising cellular material, the method comprising:
   providing a known quantity of the complex sample matrix;
   diluting said known quantity with a lysing agent, said lysing agent having an osmotic pressure lower than the osmotic pressure of the cellular material; and
   subsequently feeding the diluted known quantity through a filter including a sorbent material after a predetermined amount of time to mechanically lyse the cellular material with the sorbent material and separate Propofol from the mechanically lysed cellular material by selectively adhering the Propofol to the sorbent material.

10. The method of claim 9, wherein said method comprises using an apparatus according to claim 1, wherein:
    the known quantity of the complex sample matrix is provided at the output of the sample reception stage;
    said known quantity with a lysing agent is diluted at the mixing stage;
    the predetermined amount of time is realized by feeding said diluted known quantity through the delay stage such that said diluted known quantity has a predefined dwell time in said delay stage, said dwell time ensuring that the cellular material has at least been destabilized by the lysing agent; and
    the filter is the filter stage of said apparatus.

11. The method of claim 10, wherein the step of providing a known quantity of the complex sample matrix at the output of the sample reception stage comprises receiving an unknown quantity of the complex sample matrix at the input of the sample reception stage, separating a predefined fraction of said unknown quantity, and providing said predefined fraction as the known quantity at the output of the sample reception stage.

12. The method of claim 9, further comprising the step of flushing an eluent through said filter to dissolve Propofol in said eluent.

13. The method of claim 12, further comprising feeding said eluent into an analyte detection stage, and detecting a concentration of Propofol.

14. The method of claim 13, wherein the step of detecting a concentration of the analyte of interest comprises the steps of:
    adding a Gibbs reagent (2,6 dichloroquinone-4-chloroimide) to the eluent,
    activating the Gibbs reagent and, after the reaction between the activated Gibbs reagent and Propofol has stabilized, measuring the absorption spectrum of the reaction product of the activated Gibbs reagent and Propofol; and
    determining the concentration of Propofol in the complex sample matrix from said absorption spectrum.

15. The method of claim 12, wherein the eluent is acetonitrile.

16. The method of claim 9, further comprising the step of washing the filter with a washing agent after the step of feeding the diluted known quantity through the filter to remove material interfering with the extraction of Propofol from the sorbent material.

17. The method of claim 16, wherein the washing agent is water or a solution of methanol in water.

18. The method of claim 9, further comprising purging at least the sample reception stage, the sample mixing stage, the delay stage and the filtering stage with excess amounts of said lysing agent to purge the cellular material from said stages after the feeding of said diluted known quantity through the filtering stage.

19. The method of claim 9, further comprising pre-filtering the diluted known quantity prior to said filtering step.

20. The method of claim 9, wherein the lysing agent is selected from the group comprising de-ionized water, an aqueous salt solution, an ammonium chloride-containing solution, a detergent, urea, an acid and combinations thereof.

21. The apparatus of claim 2, wherein the metering device is a rotary valve.

22. The apparatus of claim 6, wherein the reverse sorbent material is C8, C12, C18 or Strata-X.

\* \* \* \* \*